United States Patent [19]

Lockhoff et al.

[11] Patent Number: 4,891,425
[45] Date of Patent: Jan. 2, 1990

[54] N-GLYCOSYLAMIDE DERIVATIVES, PROCESSES FOR THEIR PREPARATION AND THEIR USE AS MEDICAMENTS

[75] Inventors: Oswald Lockhoff, Cologne; Yutaka Hayauchi, Levenkusen; Peter Stadler, Haan; Helmut Brunner, Langenfeld, all of Fed. Rep. of Germany

[73] Assignee: Bayer Aktiengesellschaft, Leverkusen, Fed. Rep. of Germany

[21] Appl. No.: 7,703

[22] Filed: Jan. 28, 1987

[30] Foreign Application Priority Data

Feb. 14, 1986 [DE] Fed. Rep. of Germany ....... 3604681

[51] Int. Cl.$^4$ .................... C07H 15/12; C07H 5/06; A61K 31/70
[52] U.S. Cl. .................................................. 536/22
[58] Field of Search ..................... 514/42, 62; 536/22

[56] References Cited

U.S. PATENT DOCUMENTS

| | | | |
|---|---|---|---|
| 4,323,561 | 4/1982 | Nowotny | 514/62 |
| 4,574,122 | 3/1986 | Krüger et al. | 514/42 |
| 4,631,272 | 12/1986 | Lockhoff et al. | 536/22 |
| 4,699,899 | 10/1987 | Krüger et al. | 536/22 |
| 4,710,491 | 12/1987 | Lockhoff et al. | 536/22 |
| 4,719,202 | 1/1988 | Van Boeckel et al. | 514/62 |

FOREIGN PATENT DOCUMENTS

| | | | |
|---|---|---|---|
| 91645 | 10/1983 | European Pat. Off. | 536/22 |
| 0091645 | 10/1983 | European Pat. Off. | |
| 0100104 | 2/1984 | European Pat. Off. | |

*Primary Examiner*—Ronald W. Griffin
*Attorney, Agent, or Firm*—Sprung Horn Kramer & Woods

[57] ABSTRACT

A N-glycosylamide derivative of the formula (I)

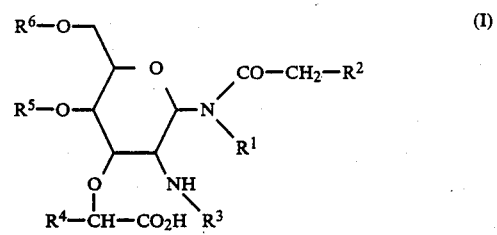

in which $R^1$ denotes hydrogen or a saturated or mono- or polyunsaturated alkyl radical with one to 50 carbon atoms,
$R^2$ denotes hydrogen or a saturated or mono- or polyunsaturated alkyl radical with one to 50 carbon atoms,
$R^3$ denotes hydrogen or an acyl radical with up to 20 carbon atoms,
$R^4$ denotes hydrogen or an alkyl radical with up to 4 carbon atoms and
$R^5$ and $R^6$ independently of one another denote hydrogen or an acyl radical with up to 10 carbon atoms or a saturated or an unsaturated alkyl radical or an aralkyl radical with up to 10 carbon atoms, or
$R^5$ and $R^6$ together denote a grouping

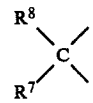

wherein $R^7$ and $R^8$ independently of one another denote hydrogen or lower alkyl with up to 5 carbon atoms or an unsubstituted or substituted aryl radical with up to 10 C atoms in the aromatic part. The N-glycosylamide derivatives exhibiting a broad defense-increasing action in the body.

21 Claims, No Drawings

N-GLYCOSYLAMIDE DERIVATIVES, PROCESSES FOR THEIR PREPARATION AND THEIR USE AS MEDICAMENTS

BACKGROUND OF THE INVENTION

The invention relates to new N-glycosylamide derivatives, processes for their preparation and their use as medicaments.

SUMMARY OF THE INVENTION

The new compounds correspond to the general formula I

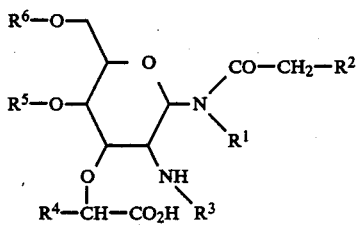

In this formulae,
- $R^1$ denotes hydrogen or a saturated or mono- or polyunsaturated alkyl radical with one to 50 carbon atoms,
- $R^2$ denotes hydrogen or a saturated or mono- or polyunsaturated alkyl radical with one to 50 carbon atoms,
- $R^3$ denotes hydrogen or an acyl radical with up to 20 carbon atoms,
- $R^4$ denotes hydrogen or an alkyl radical with up to 4 carbon atoms and
- $R^5$ and $R^6$ independently of one another denote hydrogen or an acyl radical with up to 10 carbon atoms or a saturated (alkyl) or an unsaturated radical or an aralkyl radical with up to 10 carbon atoms, or
- $R^5$ and $R^6$ together denote a grouping

wherein
$R^7$ and $R^8$ independently of one another denote hydrogen or lower alkyl with up to 5 carbon atoms or an optionally substituted aryl radical.

DETAILED DESCRIPTION OF THE INVENTION

The radical $R^1$ preferably represents a straight-chain or branched, saturated or mono- or polyunsaturated alkyl radical with up to 22 carbon atoms. Straight-chain, saturated or monounsaturated alkyl radicals with 10 to 20 carbon atoms are particularly preferred for $R^1$.

Examples of straight-chain, saturated alkyl radicals $R^1$ are methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, hexacosyl, octacosyl and triacontyl.

Examples of unsaturated alkyl radicals are vinyl, allyl, but-2-enyl, but-3-enyl, hex-2-enyl, hex-3-enyl, hex-4-enyl, hex-5-enyl, oct-2-enyl, oct-4-enyl, oct-6-enyl, dec-2-enyl, dec-4-enyl, dec-6-enyl, dec-8-enyl, dodec-2-enyl, dodec-4-enyl, dodec-6-enyl, dodec-8-enyl, dodec-10-enyl, tetradec-2-enyl, tetradec-4-enyl, tetradec-6-enyl, tetradec-8-enyl, tetradec-10-enyl, tetradec-12-enyl, hexadec-2-enyl, hexadec-4-enyl, hexadec-6-enyl, hexadec-8-enyl, hexadec-10-enyl, hexadec-12-enyl, hexadec-14-enyl, octadec-2-enyl, octadec-4-enyl, octadec-6-enyl, octadec-8-enyl, octadec-10-enyl, octadec-12-enyl, octadec-14-enyl, octadec-16-enyl, heptadec-8,11-dienyl and heptadec-8,11,14-trienyl.

The radical $R^2$ preferably represents a straight-chain or branched, saturated or mono- or diunsaturated alkyl radical with up to 22 carbon atoms, and straight-chain, saturated or monounsaturated alkyl radicals with 10 to 20 carbon atoms are particularly preferred for $R^2$. Examples of the radical $R^2$ are those mentioned under $R^1$.

The radical $R^3$ preferably represents hydrogen or a short-chain acyl radical with up to 5 carbon atoms; short-chain acyl radicals are particularly preferred.

Examples of $R^3$ are formyl, acetyl, propionyl, butyryl or valeryl.

Examples of the alkyl radicals $R^4$ are methyl, ethyl, propyl and butyl.

The radical $R^5$ preferably represents hydrogen or a short-chain, saturated acyl substituent, such as acetyl or propionyl, or an aromatic acyl substituent, such as benzoyl or p-methoxybenzoyl, or a saturated or unsaturated alkyl radical, such as allyl, or benzyl or p-methoxybenzyl. Hydrogen is a particularly preferred meaning of $R^5$.

The statements made for the radical $R^5$ apply to the radical $R^6$.

Preferred examples of those groups in which $R^5$ and $R^6$ together form a grouping

with the abovementioned meaning of $R^7$ and $R^8$ are benzylidene, p-methoxybenzylidene and isopropylidene.

As can be seen from formula I, the compounds according to the invention are based on a substituted 2-amino-2-deoxy-hexose. These amino-sugars are always bonded N-glycosidically with the acylamido group

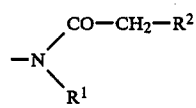

with the abovementioned meanings for $R^1$ and $R^2$, via C-1, the anomeric carbon atom.

Preferred amino-sugars in the compounds of the formula I according to the invention are 2-amino-2-deoxy-D-glucose and 2-amino-2-deoxy-D-galactose.

As can also be seen from the general formula, the C-3 hydroxyl group of the amino-sugar is etherified with an alpha-hydroxycarboxylic acid. The stereochemistry on the alpha-carbon atom of the hydroxycarboxylic acid is R or S, but the R configuration is preferred.

The invention also relates to processes for the preparation of the compounds of the general formula I according to the invention.

In these, the derivatives of the 2-amino-2-deoxyhexose acylated on the amino group, of the general formula II

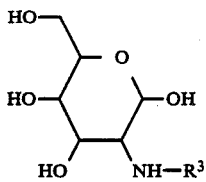

with the abovementioned meaning of $R^3$, are reacted with amino compounds $R^1$—$NH_2$, with the abovementioned meaning for $R'$, to give a glycosylamine of the general formula III

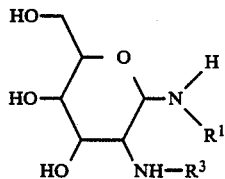

with the abovementioned meanings for $R^1$ and $R^3$. The glycosylamine of the general formula III, after being isolated, is then selectively N-acylated with a carboxylic acid derivative which is activated—as is customary with acylation reactions—to give the glycosylamide of the general formula IV

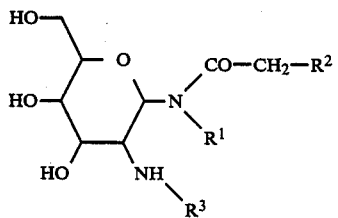

with the abovementioned meanings of $R^1$, $R^2$ and $R^3$.

The preparation of the compounds of the general formula IV is known and is described, for example, in DE-OS (German Published Specification) 3,213,650.

In the next reaction step, the compounds of the general formula IV are reacted with an aldehyde or a ketone or an aldehyde derivative or a ketone derivative to give the compounds of the general formula V.

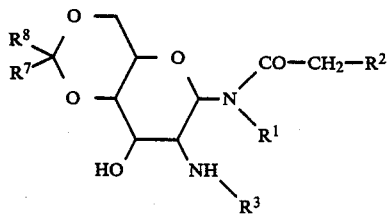

Examples of suitable aldehydes are acetaldehyde, propionaldehyde, butyraldehyde, valeraldehyde, benzaldehyde or p-methoxybenzaldehyde.

Examples of suitable ketones are acetone, methyl ethyl ketone, methyl propyl ketone, methyl butyl ketone, methyl pentyl ketone, diethyl ketone, ethyl propyl ketone or dipropyl ketone.

Suitable aldehyde derivatives are those derivatives which are already activated and which, in transacetalization reactions, react with diols to give 1,3-dioxolane rings or 1,3-dioxane rings. Suitable aldehyde derivatives are thus, for example, acetals such as acetaldehyde dimethyl acetal, acetaldehyde diethyl acetal, propionaldehyde dimethyl acetal and propionaldehyde diethyl acetal, or aromatic acetal derivatives, such as benzaldehyde dimethyl acetal and benzaldehyde diethyl acetal, or acetals which are optionally substituted in the aromatic part, such as p-tolualdehyde dimethyl acetal, p-tolualdehyde diethyl acetal, p-anisaldehyde dimethyl acetal or p-anisaldehyde diethyl acetal. Examples of suitable ketone derivatives are ketals, such as 2,2-dimethoxypropane, 2,2-diethoxypropane, 2,2-dimethoxybutane, 2,2-diethoxybutane, 2,2-dimethoxypentane, 2,2-diethoxypentane, 3,3-dimethoxypentane, acetophenone dimethyl ketal and acetophenone diethyl ketal. Suitable ketone derivatives for ketalization reactions are furthermore vinyl ethers, such as, for example, 2-propen-2-yl methyl ether.

The aldehydes or ketones or aldehyde derivatives or ketone derivatives or vinyl ethers are reacted with the triols of the general formula IV in a suitable solvent. Suitable solvents are inert organic solvents, such as, for example, tetrahydrofuran, 1,4-dioxane, dimethylformamide, methylene chloride, chloroform and ethylene glycol dimethyl ether, either as pure solvents or as mixtures with one another.

The triols of the general formula IV can also be converted into the dioxolanes of the general formula V in an excess of the aldehyde or ketone or aldehyde derivative or ketone derivative functioning as the solvent and reagent. This process variant is to be used, for example, in the preparation of 1,3-dioxanes of the general formula V in which both $R^7$ and $R^8$ represent methyl.

The aldehydes or ketones or aldehyde derivatives or ketone derivatives or vinyl ethers are reacted with the triols of the general formula V in an equivalent ratio or in up to 10-fold excess for the synthesis of the 1,3-dioxanes of the general formula V. Preferably, the triols of the formula IV are reacted with one to two equivalents of the aldehydes or ketones or the derivatives listed for these.

The synthesis of the 1,3-dioxanes of the general formula V is carried out in the presence of an acid. Suitable acids are mineral acids, such as hydrochloric acid or sulphuric acid, or hydrogen chloride, or organic acids, such as carboxylic or sulphonic acids, such as, for example, acetic acid monochloroacetic acid, dichloroacetic acid, trichloroacetic acid, trifluoroacetic acid, triphenylacetic acid, methanesulphonic acid or p-toluenesulphonic acid, or acidic ion exchange resins. The reactions to give the 1,3-dioxanes of the general formula V can be carried out in the presence of catalytic amounts to up to 0.1 molar amounts of the acid added. Catalytic amounts of acid are the preferred amounts of acid.

The synthesis of the 1,3-dioxanes of the general formula V can be carried out at temperatures from $-30°$ C. to 100° C. Temperatures ranging from 20° C. to 80° C. are preferred.

When the reaction has ended, the dioxanes of the general formula V prepared in this manner are purified and isolated by processes customary in organic chemistry, such as extraction, chromatography or crystallization.

The next step in the synthesis of the compounds of the general formula I according to the invention consists of etherification of the C-3 hydroxyl group in the compounds in the general formula V. The etherification reactions are preferably carried out with suitable alphahalogenocarboxylic acids in the presence of strong bases. Examples of suitable bases are sodium hydroxide, potassium hydroxide, barium hydroxide or sodium hydride. Examples of suitable alpha-halogenocarboxylic acids are chloroacetic acid, 2-chloropropionic acid, 2-chlorobutyric acid, 2-chlorovaleric acid, bromoacetic acid, 2-bromo-propionic acid or 2-bromovaleric acid.

The etherification for the preparation of the compounds of the general formula VI are preferably carried out in an organic, inert solvent.

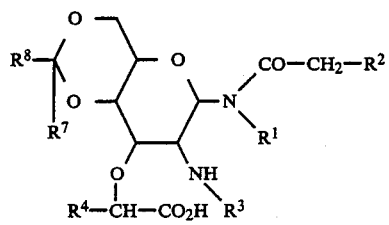
VI

Examples of suitable solvents are ethers, such as tetrahydrofuran, dioxane, ethylene glycol dimethyl ether, ethylene glycol diethyl ether and diethylene glycol dimethyl ether, amides, such as N,N-dimethylformamide and hexamethylphosphoric acid triamide, or dimethylsulphoxide.

The etherification reaction can be carried out in the temperature range from 20° C. to 100° C., and preferred reaction temperatures are between 20° C. and 70° C. The reaction times are between a few days and a few hours, depending on the temperature, base and halogenocarboxylic acid. If the reaction temperature is 60° C., sodium hydride is used as the base and 2-chloropropionic acid is used as the alkylating agent, the reaction time is about 5 hours.

The halogenocarboxylic acid can be added in a range from one to 10 equivalents, based on the alcohol, and an approximately 2- to 4-fold excess of halogenocarboxylic acid is preferred.

The reaction of the halogenocarboxylic acid with the alcohol V proceeds under Walden inversion, on the basis of the stereochemistry of the C-2 of the halogenocarboxylic acid. Thus, if an optically active 2-halogenocarboxylic acid is used as the alkylating agent, a chiral lactic acid ether is also obtained. If a L-2 halogeno-carboxylic acid is used, alkylation gives the D-lactic acid ether. The use of D-2 halogenocarboxylic acids gives L-lactic acid ethers. Enantiomer mixtures of 2-halogeno-carboxylic acids give diastereomer mixtures of the lactic acid ethers VI in question.

Reactions which are in principle similar for the synthesis of 3-O-lactyl-glucosamides which carry an oxygen-containing substituent on the C-1 of the sugar (O-glycosides) have been described several times in the literature. A current review of these activities can be found in A. Adam and E. Lederer, Med. Res. Rev., 4, 111 (1984).

The difference between the new compounds of the formula I described here and the work described in the literature reference quoted is, inter alia, that in the various work known from the literature, exclusively O-glycosides are provided with a lactic acid radical. In contrast to the O-glycosides, however, N-glycosides are converted into the 3-O-lactic acid derivatives here.

The 1,3-dioxanes of the general formula VI can be split under suitable conditions to give dialcohols of the general formula VII.

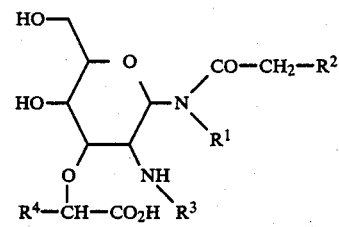
VII

Splitting reactions on 1,3-dioxanes, such as are given by 4,6,-O-isopropylidene or 4,6-O-benzylidene compounds on saccharides, are described in principle in the relevant literature, for example in "Methods in Carbohydrate Chemistry" Vol. 1, (1962), pages 69, 92, 111, 200, 201, 214, 245, 262 and 284. In the present cases for the preparation of the compounds of the general formula VII, it has proved to be advantageous to treat the 1,3-dioxanes of the general formula VI with weak, aqueous acids in a suitable diluent. Suitable solvents are halogenated hydrocarbons, such as methylene chloride and chloroform, ethers, such as 1,4-dioxane or tetrahydrofuran, alcohols, such as methanol, ethanol, propanol or isopropanol, or esters, such as ethyl acetate, either by themselves or as mixtures with one another. Tetrahydrofuran or 1,4-dioxane are in general preferably used.

Dilute aqueous acids which can be used are mineral acids, such as hydrochloric acid or sulphuric acid, or organic acids, such as acetic acid, chloroacetic acid, dichloroacetic acid, trichloroacetic acid or sulphonic acids, such as methanesulphonic acid or toluenesulphonic acid, as mixtures with water. The water content of the mixtures suitable for the splitting off reaction can be between 1 and 99%. When acetic acid is used, the preferred water content is 40 to 60%, and in the case of trifluoroacetic acid it is advantageous to carry out the reaction with a water content of 5%. It is also possible to split the 1,3-dioxane rings with acid ion exchanger resins.

The reaction temperatures for splitting the 1,3-dioxane rings in the compounds of the general formula VI are in the range from −20° C. to 90° C., depending on the splitting mixture used. The preferred temperature of the splitting reaction with aqueous acetic acid is the range from 50° C. to 70° C., and that for splitting with aqueous trifluoroacetic acid (95% strength) is room temperature.

The diols of the general formula VII could be further reacted to give the O-substituted derivatives of the general formula I.

Acylation reactions with suitable carboxylic acid derivatives, such as anhydrides or carboxylic acid chlorides, in a suitable solvent which does not participate in the reaction itself, in the presence of an inorganic or organic base, such as, for example, pyridine or triethylamine, gives the 4,6-di-O-acyl derivatives of the general formula I. Alkylations of the diols with alkyl halides in the presence of suitable bases gave the 4,6-di-O-alkyl derivatives of the general formula I

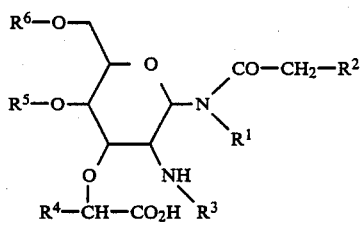
(I)
R⁵ and R⁶ = acyl or alkyl
The following synthesis scheme is intended to illustrate one of the preferred embodiments of the preparation according to the invention of compounds of the formula I by way of example.
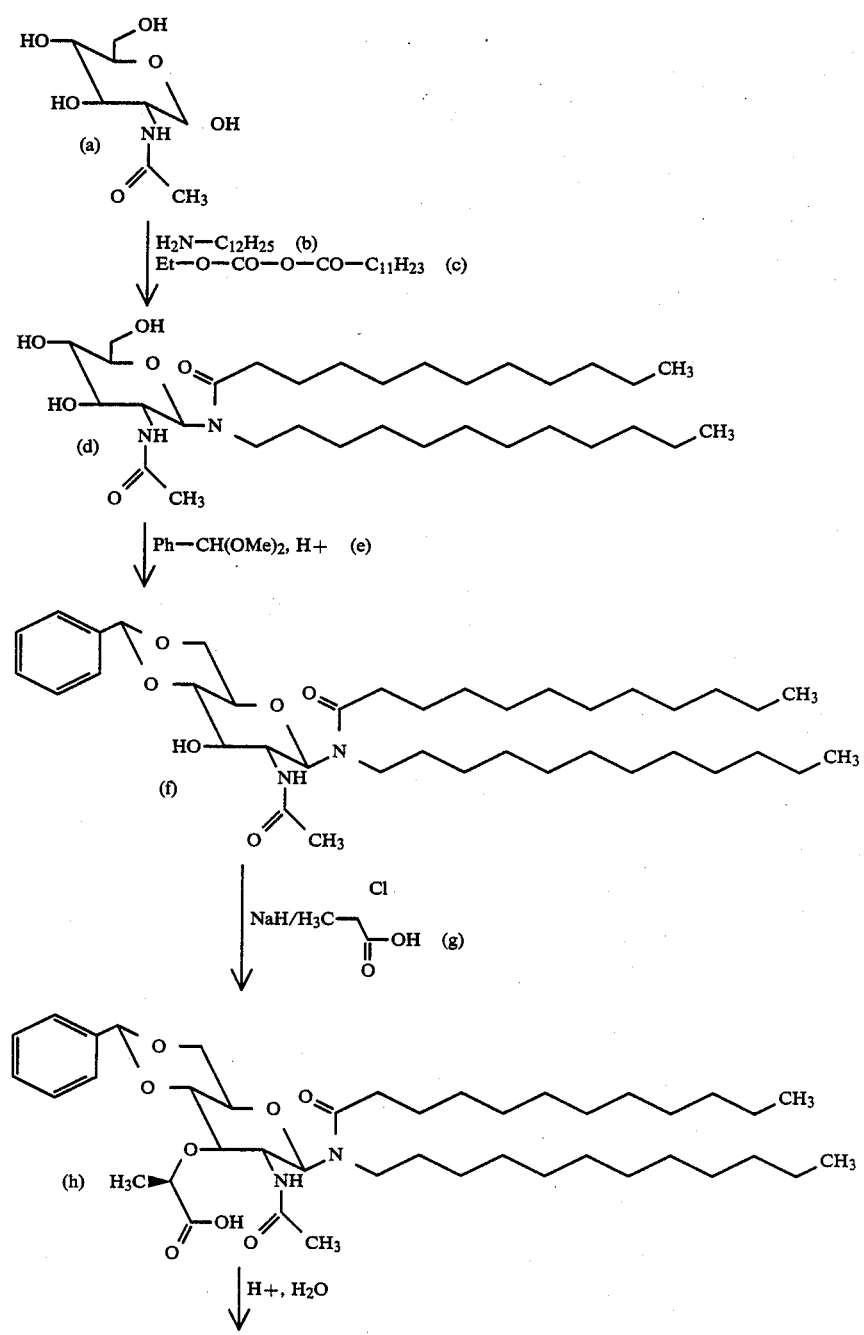

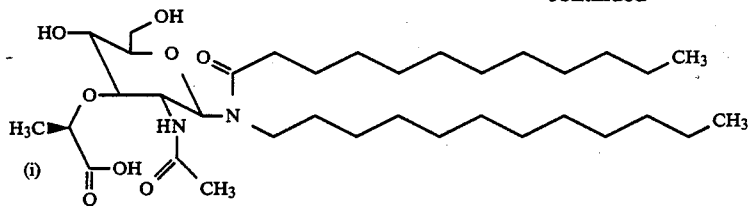

N-Acetyl-D-glucosamine (a) is reacted with dodecylamine (b) to give the glycosylamine, which is selectively N-acylated with the mixed anhydride of dodecanoic acid and ethyl chloroformate to give N-(2-acetamido-2-deoxy-β-D-glucopyranosyl)-N-dodecyl-dodecanoic acid amide (d). The triol (d) is then reacted with benzaldehyde dimethyl acetal (e) in the presence of an acid to give the benzylidene compound (f). The reaction of (f) with L-2-chloropropionic acid (g) gives the muramic acid derivative (h), with inversion on C-2 of the propionic acid. The benzylidene group in (h) could then be split off by the action of dilute aqueous acids to give the compound (i), the diol grouping of which could be either acylated or alkylated in subsequent reactions.

The invention also relates generally to the salts of the compounds of the general formula I with any other salt-forming groups, above all pharmaceutically usable, non-toxic salts, for example alkali metal or alkaline earth metal or ammonium salts.

The compounds according to the invention exhibit a broad defense-increasing action.

Substances which stimulate the endogenous defense of the body (immune system, phagocytosis) during an infection are of great interest both for human medicine and for veterinary medicine, since without assistance from endogenous defense mechanisms, many infections persist in spite of good chemotherapeutic possibilities. This can lead to recurrence of symptoms (recidivation) after coming through the first illness, and hence to chronically recurring diseases. Amongst the diseases caused by bacteria, infections with facultatively intracellular bacteria in particular present problems.

An experimental model for such a disease is infection of mice with *Salmonella typhimurium*. After inoculation of mice with these bacteria which are pathogenic to humans, a subacute to chronic disease pattern results, depending on the dose of infection, during which the animals start to die only after 4 to 7 days. During this period, there is the possibility of influencing the immune system by substances. High germ counts in the blood, liver and spleen of infected animals are found in the first two weeks. The germ counts then decrease gradually, but are still detectable 8–12 weeks after the inoculation. In infections in most other animal experiments, the animals die rapidly within 1 to 2 days. There is thus no longer any possibility of stimulating the infection defense during the infection.

It is furthermore known that N-acetyl-muramyl-L-alanyl-D-isoglutamine, the smallest active component from the cell wall of mycobacteria, stimulates non-specific infection defense (Robert Koch Stiftung e.V., Beiträge und Mitteilungen (Contributions and Communications) Vol. 5/1983, pages 31–38).

It has now been found, surprisingly, that the compounds of the general formula I according to the invention can also increase non-specific defense against infections. This was discovered with the aid of the following experiments:

The compounds of the general formula I according to the invention were administered in different doses to mice either once intraperitoneally before the infection or once daily perorally on 2 successive days, and in particular 1 day before and on the day of intraperitoneal infection with $2 \times 10^5$ colony-forming units (CFU) of *Salmonella typhimurium*. This infection dose led to a high germ count in the blood and in the organs, in particular the liver and spleen, on the 3rd day in untreated animals. The animals were housed in Makrolon cages under constant conditions ($22° \pm 2°$ C.; 55–65% relative atmospheric humidity) and received Sniff diet for experimental animals.

After treatment of the animals with the compounds of the general formula I according to the invention in dosages of 1, 10 or 100 mg/kg of active compound, a significant reduction in the germ counts in the blood of infected mice in comparison with animals which had not been treated occurred in several experiments.

These effects were found both with peroral and with parenteral administration of the substances of the general formula I. On oral or parenteral administration, they lead to a clear reduction in the bacteria count in the blood and in the liver, and in particular after intraperitoneal and intravenous infection with so-called intracellular bacteria, that is to say bacteria which, after being taken up in the macrophages—the most important cells of non-specific defense—continue to multiply until these cells are activated in the immune system and are thus put into the position of being able to destroy the bacteria intracellularly.

This will be illustrated for the substances of the formula I with the aid of compound C2 by way of example.

TABLE

| Dose (mg/kg) | Germ counts three days after the infection (% of the control) | |
|---|---|---|
| | CFU/ml of blood | CFU/g of liver |
| 10 | 4** | 25* |
| 100 | 8 | 25* |
| Control | 100% | 100% |

Differences from the control
*p = 0.05 in Student's t-test
**p < 0.01

Since the substances of the general formula I showed no direct effect in vitro on the multiplication of *Salmonella typhimurium*, it is to be assumed that the effect of the substances is based on an increase in the defence of the host against the bacteria. This leads to an increase in the survival rate of infected animals and to a more rapid subsidence of disease symptoms.

The pharmaceutical products of the present invention are preferably tablets or gelatin capsules which contain the active compounds together with diluents, for example lactose, dextrose, sucrose, mannitol, sorbitol and cellulose, and/or lubricants, for example, silica, talc, stearic acid or salts thereof, such as magnesium stearate or calcium stearate, and/or polyethylene glycol. Tablets also contain binders, for example, magnesium aluminium silicate, starches, such as corn starch, wheat starch, rice starch, arrowroot starch, gelatine, tragacanth, methylcellulose, sodium carboxymethylcellulose and/or polyvinylpyrrolidone, and, if desired, disintegrating agents, for example, starches, agar, alginic acid or a salt thereof, such as sodium alginate, and/or effervescent mixtures, or adsorbents, dyestuffs, flavoring agents and sweeteners. Injectable products are preferably isotonic aqueous solutions or suspensions. Suppositories, ointments or creams are above all fat emulsions or suspensions. The pharmaceutical products can be sterilized and/or contain auxiliaries, for example, preservatives, stabilizers, wetting agents, emulsifying agents, solubilizing agents, salts for regulating the osmotic pressure and/or buffers. The present pharmaceutical products, which, if desired, can contain other pharmacologically useful substances, are prepared in a manner which is known per se, for example by means of conventional mixing, granulating or coating processes, and contain about 0.1% to about 75%, in particular about 1% to 50%, of the active substances mentioned.

The orally administered products of the present invention can also be provided with a coating which is resistant towards gastric juice.

EXAMPLES (A) The following derivatives of the general formula IV were prepared by reacting 2-acylamino-2-deoxy-D-hexopyranose (II) with an amine $R^1$—$NH_2$ and then reacting the product with the mixed anhydride of carboxylic acid and ethyl chloroformate, according to DE-OS (German Published Specification) 3,213,650.

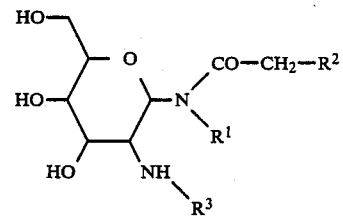

IV

| No. | $R^1$ | $R^2$ | $R^3$ | Sugar |
|---|---|---|---|---|
| A1 | —H | —$(CH_2)_{10}$—$CH_3$ | —CO—$CH_3$ | D-gluco |
| A2 | —$(CH_2)_{11}$—$CH_3$ | —$(CH_2)_{10}$—$CH_3$ | —CO—$CH_3$ | D-gluco |
| A3 | —$(CH_2)_{11}$—$CH_3$ | —$(CH_2)_{12}$—$CH_3$ | —CO—$CH_3$ | D-gluco |
| A4 | —$(CH_2)_{11}$—$CH_3$ | —$(CH_2)_{14}$—$CH_3$ | —CO—$CH_3$ | D-gluco |
| A5 | —$(CH_2)_{11}$—$CH_3$ | —$(CH_2)_{16}$—$CH_3$ | —CO—$CH_3$ | D-gluco |
| A6 | —$(CH_2)_{11}$—$CH_3$ | —$(CH_2)_{10}$—$CH_3$ | —CO—$CH_2$—$CH_3$ | " |
| A7 | —$(CH_2)_{11}$—$CH_3$ | —$(CH_2)_{10}$—$CH_3$ | —CO—$(CH_2)_2$—$CH_3$ | " |
| A8 | —$(CH_2)_{13}$—$CH_3$ | —$(CH_2)_{10}$—$CH_3$ | —CO—$CH_3$ | " |
| A9 | —$(CH_2)_{13}$—$CH_3$ | —$(CH_2)_{12}$—$CH_3$ | —CO—$CH_3$ | " |
| A10 | —$(CH_2)_{13}$—$CH_3$ | —$(CH_2)_{14}$—$CH_3$ | —CO—$CH_3$ | " |
| A11 | —$(CH_2)_{13}$—$CH_3$ | —$(CH_2)_{16}$—$CH_3$ | —CO—$CH_3$ | " |
| A12 | —$(CH_2)_{15}$—$CH_3$ | —$(CH_2)_{10}$—$CH_3$ | —CO—$CH_3$ | " |
| A13 | —$(CH_2)_{15}$—$CH_3$ | —$(CH_2)_{12}$—$CH_3$ | —CO—$CH_3$ | D-gluco |
| A14 | —$(CH_2)_{15}$—$CH_3$ | —$(CH_2)_{14}$—$CH_3$ | —CO—$CH_3$ | " |
| A15 | —$(CH_2)_{15}$—$CH_3$ | —$(CH_2)_{16}$—$CH_3$ | —CO—$CH_3$ | " |
| A16 | —$(CH_2)_{17}$—$CH_3$ | —$(CH_2)_{10}$—$CH_3$ | —CO—$CH_3$ | " |
| A17 | —$(CH_2)_{17}$—$CH_3$ | —$(CH_2)_{12}$—$CH_3$ | —CO—$CH_3$ | " |
| A18 | —$(CH_2)_{17}$—$CH_3$ | —$(CH_2)_{14}$—$CH_3$ | —CO—$CH_3$ | " |
| A19 | —$(CH_2)_{17}$—$CH_3$ | —$(CH_2)_{16}$—$CH_3$ | —CO—$CH_3$ | " |
| A20 | —$(CH_2)_{11}$—$CH_3$ | —$(CH_2)_{16}$—$CH_3$ | —CO—$CH_3$ | " |
| A21 | —$(CH_2)_{13}$—$CH_3$ | —$(CH_2)_{16}$—$CH_3$ | —CO—$CH_3$ | D-galacio |
| A22 | —$(CH_2)_{15}$—$CH_3$ | —$(CH_2)_{16}$—$CH_3$ | —CO—$CH_3$ | " |
| A23 | —$(CH_2)_{17}$—$CH_3$ | —$(CH_2)_{16}$—$CH_3$ | —CO—$CH_3$ | " |

(B) General process for the preparation of the 1,3-dioxane derivatives of the formula V. ($R^7$=phenyl, $R^8$=H)

25 mmol of the triol of the general formula IV were dissolved in 100 ml of absolute tetrahydrofuran, 27.5 mmol of benzaldehyde dimethyl acetal and 10 mg of p-toluenesulphonic acid were added and the mixture was heated at 60° C. for several hours. The progress of the reaction was monitored by thin layer chromatography on silica gel (mobile phase: toluene/ethanol=5:1). When the reaction had ended, the acid was neutralized with a basic ion exchanger resin. The resin was filtered off, the filtrate was evaporated in vacuo and, after being taken up twice in toluene, the mixture was evaporated again to a syrup. Crystallization from petroleum ether. Yield about 75–95%.

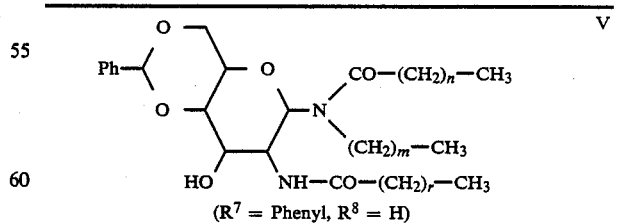

($R^7$ = Phenyl, $R^8$ = H)

| No. | Config[a] | m | n | r | Rf[b] | Melting point | $[\alpha]_D$ |
|---|---|---|---|---|---|---|---|
| B1 | D-glc | (d) | (d) | 0 | | | |
| B2 | D-glc | 11 | 10 | 0 | 0.19 | 124° | −0.2° |
| B3 | D-glc | 11 | 12 | 0 | 0.20 | 119 | |
| B4 | D-glc | 11 | 14 | 0 | 0.19 | 120 | −0.2° |
| B5 | D-glc | 11 | 16 | 0 | 0.20 | 119 | +0.1° |

-continued

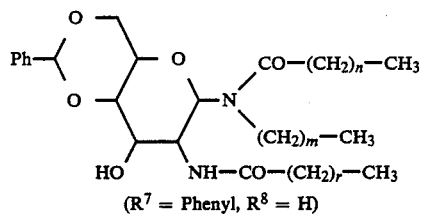

($R^7$ = Phenyl, $R^8$ = H)

| No. | Config(a) | m | n | r | Rf(b) | Melting point | $[\alpha]_D$ |
|---|---|---|---|---|---|---|---|
| B6  | D-glc | 11 | 10 | 1 | | | |
| B7  | D-glc | 11 | 10 | 2 | | | |
| B8  | D-glc | 13 | 10 | 0 | 0.18 | 126 | +0.8° |
| B9  | D-glc | 13 | 12 | 0 | 0.18 | 120 | −0.4° |
| B10 | D-glc | 13 | 14 | 0 | | | |
| B11 | D-glc | 13 | 16 | 0 | 0.19 | 119 | +0.5° |
| B12 | D-glc | 15 | 10 | 0 | | | |
| B13 | D-glc | 15 | 12 | 0 | | | |
| B14 | D-glc | 15 | 14 | 0 | | | |
| B15 | D-glc | 15 | 16 | 0 | | | |
| B16 | D-glc | 17 | 10 | 0 | 0.18 | 117 | 0.6° |
| B17 | D-glc | 17 | 12 | 0 | 0.20 | 112 | −0.4° |
| B18 | D-glc | 17 | 14 | 0 | | | |
| B19 | D-glc | 17 | 16 | 0 | 0.21 | 119 | −0.6° |
| B20 | D-gal | 11 | 16 | 0 | | | |
| B21 | D-gal | 13 | 16 | 0 | | | |
| B22 | D-gal | 15 | 16 | 0 | | | |
| B23 | D-gal | 17 | 16 | 0 | | | |

(a)D-glc: D-glutose; D-gal: D-galactose
(b)Mobile phase: toluene/acetone = 3:1
(c)Solvent: tetrahydrofuran
(d)C-1 substituent on the sugar: —NH—CO—$(CH_2)_{10}$—$CH_3$ (c) General process for the preparation of the D-Lactic acid ethers of the general formula VI.

30.0 mmol of the dioxane compound of the general formula V were dissolved in 800 ml of 1,4-dioxane and, after addition of 150 mmol of sodium hydride, the mixture was warmed to 95° C. After 5 minutes, the mixture was cooled to 60° C. 110 mmol of L-2-chloropropionic acid, dissolved in 50 ml of 1,4-dioxane, were added dropwise to the batch. The reaction temperature was kept at 60° C. for several hours. The progress of the reaction was monitored by thin layer chromatography on silica gel (mobile phase: toluene/ethanol=5:1).

When the reaction had ended, the excess of sodium hydride was decomposed by careful addition of 2-propanol, and the mixture was then poured onto ice-water and brought to pH 2.5 with 1N hydrochloric acid. The aqueous phase was extracted with 500 ml of ether and the ether phases were extracted back twice with 100 ml of water each time. The ether phase was dried over magnesium sulphate and evaporated to a syrup. The resulting residue was crystallized from methanol. Yields about 70–90%.

The following derivatives were prepared in accordance with these instructions:

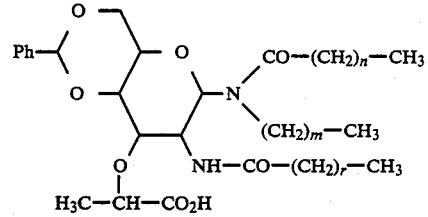

($R^7$ = Phenyl, $R^8$ = H, $R^4$ = $CH_3$)

| No. | Config(a) | m | n | r | Rf(b) | Melting point | $[\alpha]_D^{(c)}$ |
|---|---|---|---|---|---|---|---|
| C1  | D-glc | (d) | (d) | 0 | | | |
| C2  | "     | 11 | 10 | 0 | 0.36 | 130° | +5.5° |
| C3  | "     | 11 | 12 | 0 | 0.36 | 117° | +5.2° |
| C4  | "     | 11 | 14 | 0 | 0.37 | 130° | +5.4° |
| C5  | "     | 11 | 16 | 0 | 0.41 | 127° | +5.6° |
| C6  | "     | 11 | 10 | 1 | | | |
| C7  | "     | 11 | 10 | 2 | | | |
| C8  | "     | 13 | 10 | 0 | 0.35 | 143° | +5.4° |
| C9  | "     | 13 | 12 | 0 | 0.36 | 130° | +5.5° |
| C10 | "     | 13 | 14 | 0 | | | |
| C11 | "     | 13 | 16 | 0 | 0.39 | 107° | +5.6° |
| C12 | "     | 15 | 10 | 0 | | | |
| C13 | "     | 15 | 12 | 0 | | | |
| C14 | "     | 15 | 14 | 0 | | | |
| C15 | "     | 15 | 16 | 0 | | | |
| C16 | "     | 17 | 10 | 0 | 0.38 | 114° | +4.7° |
| C17 | "     | 17 | 12 | 0 | 0.38 | 117° | +4.7° |
| C18 | "     | 17 | 14 | 0 | | | |
| C19 | "     | 17 | 16 | 0 | 0.40 | 108° | +4.9° |
| C20 | D-gal | 11 | 16 | 0 | | | |
| C21 | "     | 13 | 16 | 0 | | | |
| C22 | "     | 15 | 16 | 0 | | | |
| C23 | "     | 17 | 16 | 0 | | | |

(a)D-glc: D-glucose; D-gal: D-galactose
(b)Mobile phase toluene/ethanol = 3:1
(c)Solvent: tetrahydrofuran
(d)C-1 substituent on the sugar: —NH—CO—$(CH_2)_{10}$—$CH_3$ The following compounds were prepared in accordance with the abovementioned general instructions for the preparation of the compounds of the formula VI, using different 2-halogenocarboxylic acids to L-2-chloropropionic acid:

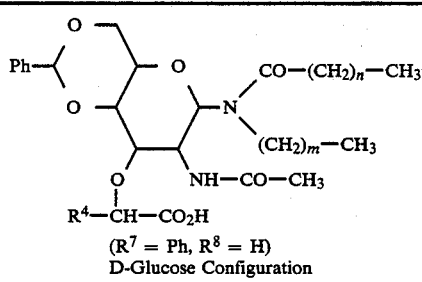

($R^7$ = Ph, $R^8$ = H)
D-Glucose Configuration

| No. | m | n | acid used | $R^4$ | Rf(a) |
|---|---|---|---|---|---|
| C24 | 11 | 10 | Br—$CH_2$—$CO_2H$ | H | 0.35 |
| C25 | 11 | 16 | Br—$CH_2$—$CO_2H$ | H | 0.37 |
| C26 | 13 | 16 | Br—$CH_2$—$CO_2H$ | H | |
| C27 | 17 | 16 | Br—$CH_2$—$CO_2H$ | H | 0.37 |
| C28 | 11 | 10 | $H_5C_2$—CH(Br)—$CO_2H$(b) | $C_2H_5$ | 0.37 |
| C29 | 17 | 10 | $H_5C_2$—CH(Br)—$CO_2H$ | $C_2H_5$ | 0.38 |

(a)Mobile phase toluene : ethanol = 3:1
(b)Enantiomer mixture
(D) General instructions for the preparation of the diols of the general formula VII.

10 mmol of the 1,3-dioxane compound of the general formula VI were dissolved in 150 ml of glacial acetic acid and the solution was warmed to 80° C. 20 ml of water were added dropwise to the mixture and heating of the reaction mixture was continued at 80° C. The progress of the reaction was monitored by thin layer chromatography on silica gel (mobile phase toluene/ethanol/glacial acetic acid=10:2:0.15). After about 3 hours, the mixture was cooled to room temperature. The colorless solid which then precipitated out was filtered off with suction, washed with water and dried.

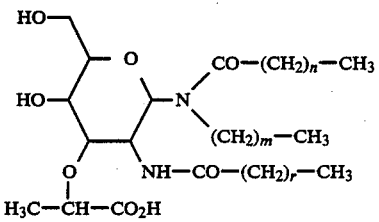

VI

| No. | Config.[a] | m | n | r | Rf[b] | [α][c] |
|---|---|---|---|---|---|---|
| D1 | D-glc | [d] | [d] | 0 | | |
| D2 | " | 11 | 10 | 0 | 0.24 | +23.3° |
| D3 | " | 11 | 12 | 0 | 0.24 | +23.2° |
| D4 | " | 11 | 14 | 0 | 0.25 | +22.5° |
| D5 | " | 11 | 16 | 0 | 0.25 | +20.3° |
| D6 | " | 11 | 10 | 1 | | |
| D7 | " | 11 | 10 | 2 | | |
| D8 | " | 13 | 10 | 0 | 0.23 | +22.4° |
| D9 | " | 13 | 12 | 0 | 0.23 | +22.9° |
| D10 | " | 13 | 14 | 0 | | |
| D11 | " | 13 | 16 | 0 | 0.24 | +23.4° |
| D12 | " | 15 | 10 | 0 | | |
| D13 | " | 15 | 12 | 0 | | |
| D14 | " | 15 | 14 | 0 | | |
| D15 | " | 15 | 16 | 0 | | |
| D16 | " | 17 | 10 | 0 | 0.24 | +22.8° |
| D17 | " | 17 | 12 | 0 | 0.25 | +22.1° |
| D18 | " | 17 | 14 | 0 | | |
| D19 | " | 17 | 16 | 0 | 0.26 | +21.5° |
| D20 | D-gal | 11 | 16 | 0 | | |
| D21 | " | 13 | 16 | 0 | | |
| D22 | " | 15 | 16 | 0 | | |
| D23 | " | 17 | 16 | 0 | | |

[a] D-glc: D-glucose; D-gal: D-galactose
[b] Mobile phase: toluene/ethanol/glacial acetic acid = 10:2:0.15
[c] Solvent: tetrahydrofuran
[d] C-1 substituent on the sugar: —NH—CO(CH$_2$)$_{10}$—CH$_3$ The compounds C 24 to C 29 were also converted into the diols of the formula VI under the same conditions.

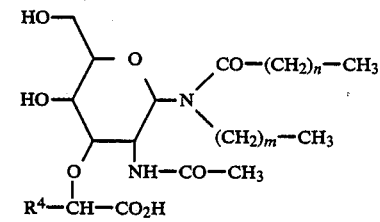

| No. | m | n | R$^4$ | Rf[a] |
|---|---|---|---|---|
| D24 | 11 | 10 | H | 0.24 |
| D25 | 11 | 16 | H | 0.25 |
| D26 | 13 | 16 | H | 0.24 |
| D27 | 17 | 16 | H | 0.25 |
| D28 | 11 | 10 | C$_2$H$_5$ | 0.26 |
| D29 | 17 | 10 | C$_2$H$_5$ | 0.26 |

[a] Mobile phase toluene/ethanol/glacial acetic acid = 10:2:0.15

It will be appreciated that the instant specification and claims are set forth by way of illustration and not limitation, and that various modifications and changes may be made without departing from the spirit and scope of the present invention.

What is claimed is:

1. A compound of the formula (I)

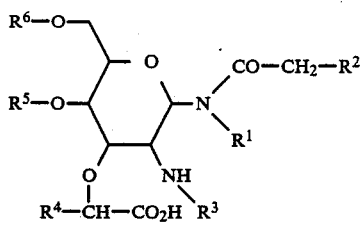

in which
$R^1$ denotes hydrogen or a saturated or mono- or polyunsaturated alkyl radical with one to 50 carbon atoms,
$R^2$ denotes hydrogen or a saturated or mono- or polyunsaturated alkyl radical with one to 50 carbon atoms,
$R^3$ denotes hydrogen or an acyl radical with up to 20 carbon atoms, said acyl radical being selected from the group consisting of formyl, acetyl, propionyl, butyryl and valeryl,
$R^4$ denotes hydrogen or an alkyl radical with up to 4 carbon atoms and
$R^5$ and $R^6$ independently of one another denote hydrogen or an acyl radical with up to 10 carbon atoms, said acyl radical being selected from the group consisting of formyl, acetyl, propionyl, butyryl, valeryl, benzoyl and p-methoxybenzoyl, an alkyl or a saturated or unsaturated radical or an aralkyl with up to 10 carbon atoms, or
$R^5$ and $R^6$ together denote a grouping

wherein
$R^7$ and $R^8$ independently of one another denote hydrogen or lower alkyl with up to 5 carbon atoms or an unsubstituted or substituted aryl radical with up to 10 carbon atoms in the aromatic part, or a physiologically acceptable salt thereof.

2. A compound according to claim 1, wherein
$R^1$ and $R^2$ represent a straight-chain, saturated or mono- or polyunsaturated alkyl radical with up to 22 carbon atoms,
$R^3$ denotes hydrogen or a short-chain acyl radical with up to 5 carbon atoms, said acyl radical being selected from the group consisting of formyl, acetyl, propionyl, butyryl and valeryl, or, represents an unsaturated radical with up to 5 carbon atoms,
$R^5$ and $R^6$ together form a benzylidene, p-methoxybenzylidene or isopropylidene group.

3. A compound according to claim 1, wherein for $R^5$ or $R^6$ the acyl radical is selected from the group consisting of benzoyl and p-methoxybenzoyl.

4. A compound according to claim 1, wherein
$R^1$ and $R^2$ independently of one another represent straight-chain, saturated or monounsaturated alkyl radicals with 10 to 20 carbon atoms, R³ represents formyl, acetyl, propionyl, butyryl or valeryl and R⁴ denotes methyl, ethyl, n-propyl, i-propyl or butyl.

5. A compound according to claim 1, wherein R¹ and R² are identical or different and represent methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, hexacosyl, octacosyl, triacontyl, vinyl, allyl, but-2-enyl, but-3-enyl, hex-2-enyl, hex-3-enyl, hex-4-enyl, hex-5-enyl, oct-2-enyl, oct-4-enyl, oct-6-enyl, dec-2-enyl, dec-4-enyl, dec-6-enyl, dec-8-enyl, dodec-2-enyl, dodec-4-enyl, dodec-6-enyl, dodec-8-enyl, dodec-10-enyl, tetradec-2-enyl, tetradec-4-enyl, tetradec-6-enyl, tetradec-8-enyl, tetradec-10-enyl, tetradec-12-enyl, hexadec-2-enyl, hexadec-4-enyl, hexadec-6-enyl, hexadec-8-enyl, hexadec-10-enyl, hexadec-12-enyl, hexadec-14-enyl, octadec-2-enyl, octadec-4-enyl, octadec-6-enyl, octadec-8-enyl, octadec-10-enyl, octadec-12-enyl, octadec-14-enyl, octadec-16-enyl, heptadec-8,11-dienyl or heptadec-8,11,14-trienyl.

6. A compound according to claim 1, wherein the formula (I) contains a sugar residue selected from the group consisting of a 2-amino-2-deoxy-D-glucose residue and a 2-amino-2-deoxy-D-galactose residue.

7. A compound according to claim 1, having the formula (F)

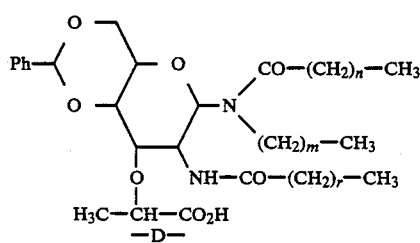

wherein
the compound is selected from the group consisting of
(a) a compound of formula F with a D-glucose configuration and m=11, n=10 and r=0;
(b) a compound of the formula F with a D-glucose configuration and m=11, n=12 and r=0;
(c) a compound of the formula F with a D-glucose configuration and m=11, n=16 and r=0;
(d) a compound of the formula F with a D-glucose configuration and m=13, n=10 and r=0;
(e) a compound of the formula F with a D-glucose configuration and m=17, n=10 and r=0; and
(f) a compound of the formula F with a D-galactose configuration and m=11, n=16 and r=0.

8. A compound according to claim 1 having the formula

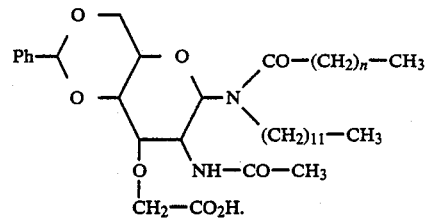

9. A compound according to claim 1 having the formula (G) of a D-glucose configuration

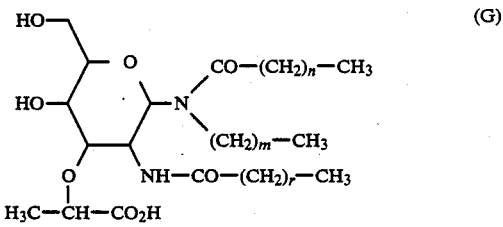

wherein the compound is selected from the group consisting of
(a) a compound of the formula G with m=11, n=10 and r=0;
(b) a compound of the formula G with m=11, n=10 and r=1 and
(c) a compound of the formula G with m=17, n=10 and r=0.

10. A compound according to claim 1, wherein R⁵ and R⁶ independently of one another represent benzyl or p-methoxybenzoyl.

11. A process for the preparation of a compound of the formula (I)

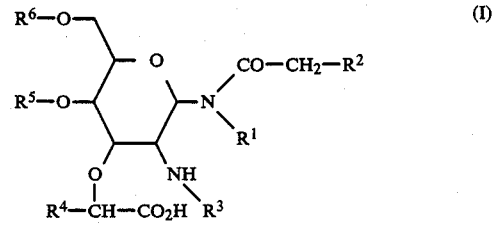

in which
R¹ denotes hydrogen or a saturated or mono- or polyunsaturated alkyl radical with one to 50 carbon atoms,
R² denotes hydrogen or a saturated or mono- or polyunsaturated alkyl radical with one to 50 carbon atoms,
R³ denotes hydrogen or an acyl radical with up to 20 carbon atoms,
R⁴ denotes hydrogen or an alkyl radical with up to 4 carbon atoms and
R⁵ and R⁶ independently of one another denote hydrogen or an acyl radical with up to 10 carbon atoms or an optionally unsaturated alkyl radical or an aralkyl radical with up to 10 carbon atoms,
R⁶ denotes hydrogen or an acyl radical with up to 10 carbon atoms or an alkyl radical with up to 10 carbon atoms, or
R⁵ and R⁶ together denote a grouping

wherein

R⁷ and R⁸ independently of one another denote hydrogen or lower alkyl with up to 5 carbon atoms or an unsubstituted or substituted aryl radical with up to 10 C atoms in the aromatic part, comprising reacting a derivative of a 2-amino-2-deoxyhexoses acylated on the amino group, of the formula (II)

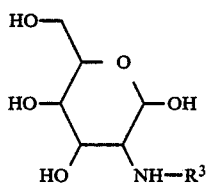

with abovementioned meaning of $R^3$, with an amino compound $R^1$—NH₂, with the abovementioned meaning for R', to yield a glycosylamine of the formula (III)

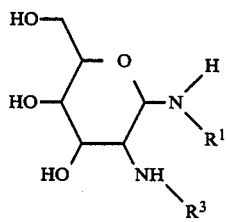

with the abovementioned meanings for $R^1$ and $R^3$, isolating the glycosylamine of the formula (III), selectively N-acylating the glycosylamine with an activated carboxylic acid derivative to yield a glycosylamine of the formula (IV)

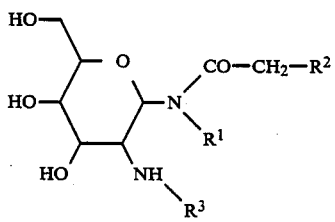

with the abovementioned meanings of $R^1$, $R^2$ and $R^3$, reacting the compound of the formula (IV) with an aldehyde, a ketone, an aldehyde derivative or a ketone derivative to yield a dioxane of the formula (V)

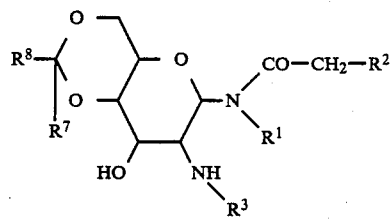

purifying or isolating the dioxane, etherifying the C-3 hydroxyl group in the dioxane compound of the formula (V) to yield a 1,3-dioxane compound of the formula (VI)

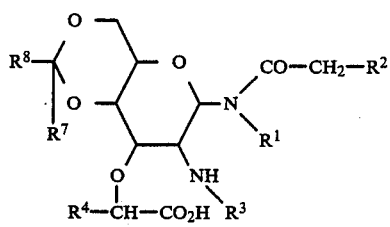

splitting the 1,3-dioxane of the formula (VI) to yield a dialcohol of the formula (VII)

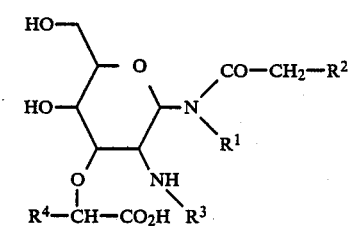

and acylating or alkylating the alcohol of formula VII to yield the compound of the formula I.

12. A process according to claim 11, wherein the compound of the formula (VI) is reacted with acetone, methyl ethyl ketone, methyl propyl ketone, methyl butyl ketone, methyl pentyl ketone, diethyl ketone, ethyl propyl ketone or dipropyl ketones or with acetaldehyde dimethyl acetal, acetaldehyde diethyl acetal, propionaldehyde dimethyl acetal, propionaldehyde diethyl acetal, benzaldehyde dimethyl acetal, benzaldehyde diethyl acetal, such as p-toluenealdehyde dimethyl acetal, p-toluenedehyde diethyl acetal or p-anisaldehyde dimethyl acetal, p-anisaldehyde diethyl acetal, 2,2-dimethoxypropane, 2,2-diethoxypropane, 2,2-dimethoxybutane, 2,2-diethoxybutane, 2,2-dimethoxypentane, 2,2-diethoxypentane, 3,3-dimethoxypentane, 3,3-diethoxypentane, acetophenone dimethyl ketal, acetophenone diethyl ketal or 2-peopen-2-yl methyl ether, to yield a compound of the formula (V).

13. A process according to claim 11, wherein in the reaction of the glycosylamide to yield the dioxane is carried out in tetrahydrofuran, 1,4-dioxane, dimethylformamide, methylene chloride, chloroform or ethylene glycol dimethyl ether, or in mixtures thereof, or in an excess of the aldehyde or ketone or aldehyde derivative or ketone derivative functioning both as a solvent or a reagent.

14. A process according to claim 11, wherein the reaction of the compound of the formula (IV) to yield the compound of the formula (V) is carried out with a 1- to 10-fold excess of aldehyde or ketone or derivatives thereof in the presence of catalytic to 0.1 molar amounts of an acid selected from the group consisting of acetic acid, monochloroacetic acid, dichloroacetic acid, trichloroacetic acid, trifluoroacetic acid, triphenylacetic acid, methanesulphonic acid and p-toluenesulphonic acid, or in the presence of an acid ion exchanger.

15. A process according to claim 11, wherein the reaction is carried out at temperatures from $-30°$ C. to $100°$ C.

16. A process according to claim 11, wherein the etherification reaction to yield the compound of the formula (VI) is carried out at temperatures from $20°$ C. to $100°$ C. with 1 to 10 equivalents of an alpha-halogenocarboxylic acid in the presence of a strong base.

17. A process according to claim 11, wherein the 1,3-dioxane of the formula (VI) is split in methylene chloride, chloroform, 1,4-trioxane, tetrahydrofuran, methanol, ethanol, propanol, isopropanol or ethyl acetate or in mixtures thereof in the presence of an aqueous, weak acid to yield the compound of the formula (VII).

18. A process according to claim 11, wherein the compound of the formula (VII) is reacted with a carboxylic acid derivative or an alkyl halide in the presence of a base to yield a 4,6-tri-O-acyl derivative or a 4,6-tri-O-alkyl derivative of the formula (I).

19. A process according to claim 11, wherein the purifying or isolating is carried out by extraction, chromatography or crystallization.

20. A method of stimulating the endogenous defense which comprises administering an effective amount of a compound according to claim 1.

21. An immunostimulating composition comprising an immunostimulating effective amount of a compound according to claim 1 in admixture with a pharmaceutically acceptable carrier.

* * * * *